United States Patent
Xiao (10) Patent No.: US 10,543,391 B2
(45) Date of Patent: Jan. 28, 2020

(54) EXERCISE DEVICE AND UPRIGHT POSTURE RETAINER FOR UPPER BODY

(71) Applicant: Ji Xiao, Alhambra, CA (US)

(72) Inventor: Ji Xiao, Alhambra, CA (US)

(*) Notice: Subject to any disclaimer, the term of this patent is extended or adjusted under 35 U.S.C. 154(b) by 193 days.

(21) Appl. No.: 15/641,204

(22) Filed: Jul. 3, 2017

(65) Prior Publication Data

US 2018/0001129 A1 Jan. 4, 2018

Related U.S. Application Data

(60) Provisional application No. 62/493,369, filed on Jul. 1, 2016.

(51) Int. Cl.
| | |
|---|---|
| A63B 21/045 | (2006.01) |
| A63B 21/04 | (2006.01) |
| A63B 23/02 | (2006.01) |
| A63B 23/04 | (2006.01) |

(52) U.S. Cl.
CPC ............ *A63B 21/045* (2013.01); *A63B 21/04* (2013.01); *A63B 23/0233* (2013.01); *A63B 23/0482* (2013.01)

(58) Field of Classification Search
CPC ..... A63B 21/04; A63B 21/045; A63B 21/026; A63B 21/4025; A63B 21/00189; A63B 21/4005; A63B 23/0233; A63B 23/0238; A61H 2201/1623; A61H 2201/1626; A61H 2230/62; A61F 5/0102
See application file for complete search history.

(56) References Cited

U.S. PATENT DOCUMENTS

| | | | | | |
|---|---|---|---|---|---|
| 1,202,851 | A | * | 10/1916 | Kelly | A61F 5/028 2/44 |
| 4,428,577 | A | * | 1/1984 | Weingardt | A63B 21/00043 482/126 |
| 4,541,419 | A | * | 9/1985 | Osawa | A61F 5/026 602/19 |
| 5,176,622 | A | * | 1/1993 | Anderson | A61F 5/02 482/124 |
| 5,709,648 | A | * | 1/1998 | Webb | A61F 5/026 2/44 |
| 5,716,307 | A | * | 2/1998 | Vadher | A43B 7/20 482/124 |

(Continued)

*Primary Examiner* — Nyca T Nguyen
(74) *Attorney, Agent, or Firm* — Raymond Y. Chan; David and Raymond Patent Firm (57) ABSTRACT

An upright posture retainer for upper body includes two upright retaining frames, and an adjusting device connected with the upright retaining frames and adjusted a distance between the upright retaining frames; wherein each of the upright retaining frames includes a resilient longitudinal retaining frame extended longitudinally and tending to recover an original upright state under stress, a shoulder retaining member and a leg retaining frame, wherein the shoulder retaining member is extended from an upper end of the resilient longitudinal retaining frame so as to form a shoulder contacting space, wherein the leg retaining frame is extended from an lower end of the resilient longitudinal retaining frame and transversely extended to form a leg retaining space, thereby contacting with the front of the human leg; wherein the adjusting device is fixed to the resilient longitudinal retaining frames of the upright retaining frames and supports the rear of upper body.

20 Claims, 9 Drawing Sheets

(56) References Cited

U.S. PATENT DOCUMENTS

| | | | | |
|---|---|---|---|---|
| 5,772,563 | A * | 6/1998 | Lin | A63B 23/0211 |
| | | | | 482/121 |
| 6,905,447 | B1 * | 6/2005 | Walter | A61H 1/0292 |
| | | | | 482/121 |
| 7,585,261 | B2 * | 9/2009 | Serlachius | A63B 21/04 |
| | | | | 482/130 |
| 2007/0074327 | A1 * | 4/2007 | Davies | A61F 5/026 |
| | | | | 2/44 |
| 2008/0228121 | A1 * | 9/2008 | Hughes | A61F 5/026 |
| | | | | 602/35 |
| 2011/0098617 | A1 * | 4/2011 | Ferguson | A61F 5/026 |
| | | | | 602/16 |
| 2012/0184881 | A1 * | 7/2012 | Kobayashi | A61F 5/01 |
| | | | | 601/33 |
| 2016/0250062 | A1 * | 9/2016 | Radaelli | A61F 5/02 |
| | | | | 602/16 |
| 2016/0317340 | A1 * | 11/2016 | Jangir | A61H 3/00 |

\* cited by examiner

EXERCISE DEVICE AND UPRIGHT POSTURE RETAINER FOR UPPER BODY

CROSS REFERENCE OF RELATED APPLICATION

This is a non-provisional application that claims the benefit of priority under 35 U.S.C. § 120 to a provisional application, application No. 62/493,369, filed Jul. 1, 2016, which is incorporated herewith by reference in its entity.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to exercise device, and more particularly to an exercise device that not only can be putted on the body of exerciser helping him or her to exercise by their body movements, such as walking and jogging, but also can be worked as an upright posture retainer for upper body.

Description of Related Arts

The modern social environment becomes more and more complex; as a result, a healthy body is very important. In order to obtain and to maintain a body with good health, proper exercise is necessary for people. People exercise in a variety of ways to get a healthy body. On one hand, some exercises are relatively simple, such as jogging and hiking. On the other hand, in order to achieve a better fitness effect, people often use a variety of fitness equipment to assist the movement. There are many varieties of fitness equipment, and the styles and functions thereof are different. The space occupied is also not the same. In order to use the fitness equipment to exercise, people chooses to go to the gym instead of placing the fitness equipment with a large volume which may occupy too much family space.

Fitness equipment for the gym is very helpful for the exercise; however, people cannot go to the gym at anytime and anywhere to keep fitness. The gym also has a certain time for business, and the air ventilation inside the gym is not good. What people need is not only a simple way to achieve a good exercise, but also to get a good fitness effect in the exercise.

In addition, on one hand, the development of modern network information technology conveniences people's modern life. However, on the other hand, the development of modern network information technology results in a lot of people needing to work for a long time and sitting in the office chair. The general structure of the office chair cannot fully support people's body, when people is at work and sit in the office chair, the waist and back are in a tight and vacant state, the waist cannot be supported, and the back is easy to bend. Long and sedentary work is also a great threat for people's health. Therefore, under a condition that the office chair cannot be replaced in a timely manner, people needs a device to support and protect the people's waist and back, thereby easing people's sedentary fatigue.

In addition, the tense working environment in modern society makes people have to work longer and longer and the general office does not provide a place to rest. In the work gap, people need a short break; they have to put the head lying on the desk to rest. This position does not ease people's fatigue, and even increase the burden on the body. Therefore, there is need for people to have a device to enable people for a short break in a limited space office environment and make the body get support to ease fatigue.

In addition, as one of human natures, people tend to hunch to obtain the most comfortable posture, especially when they have to seat; because of the force of gravity, the human body is tended to attracted to the ground and the skeleton have to fight against the tendency. However, long-time hunching results the deformation of the skeleton, especially the spine. Therefore, there is a need for people to have a convenient, portable and effective body corrector.

SUMMARY OF THE PRESENT INVENTION

The invention is advantageous in that it provides an upright posture retainer for upper body, which put on the body of exerciser helping them to exercise by their body movements, such as walking or jogging.

Another advantage of the invention is to provide an upright posture retainer for upper body, which is capable of retaining a human body in an upright posture.

Another advantage of the invention is to provide an upright posture retainer for upper body, which is capable of exercising human muscles.

Another advantage of the invention is to provide an upright posture retainer for upper body, which provided a resilient longitudinal retaining frame to retain an upright posture of human upper body.

Another advantage of the invention is to provide an upright posture retainer for upper body, which provides an opposite acting force against the movement of human legs, thereby exercising leg muscles.

Another advantage of the invention is to provide an upright posture retainer for upper body, which is used as a convenient and portable exercise equipment.

Another advantage of the invention is to provide an upright posture retainer for upper body, which is used as a seating position equipment.

Another advantage of the invention is to provide an upright posture retainer for upper body, which is used as a backrest and supports human backs and waists.

Another advantage of the invention is to provide an upright posture retainer for upper body, which is capable of preventing people from hunching.

Another advantage of the invention is to provide an upright posture retainer for upper body, which is used as a nap assisting equipment.

Another advantage of the invention is to provide an upright posture retainer for upper body, which has a simple structure and is portable to be carried and to be received.

Additional advantages and features of the invention will become apparent from the description which follows, and may be realized by means of the instrumentalities and combinations particular point out in the appended claims.

According to the present invention, the foregoing and other objects and advantages are attained by a n upright posture retainer for upper body, comprising:

a pair of upright retaining frames, and an adjusting device connected with the upright retaining frames and adjusted a distance between the upright retaining frames;

wherein each of the upright retaining frames comprises a resilient longitudinal retaining frame extended longitudinally and tending to recover an original upright state under stress, a shoulder retaining member and a leg retaining frame, wherein the shoulder retaining member is extended from an upper end of the resilient longitudinal retaining frame so as to form a shoulder contacting space, wherein the leg retaining frame is extended from an lower end of the resilient longitudinal retaining frame and transversely extended to form a leg retaining space, thereby contacting with the front of the human leg;

wherein the adjusting device is fixed to the resilient longitudinal retaining frames of the upright retaining frames and supports the rear of upper body.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
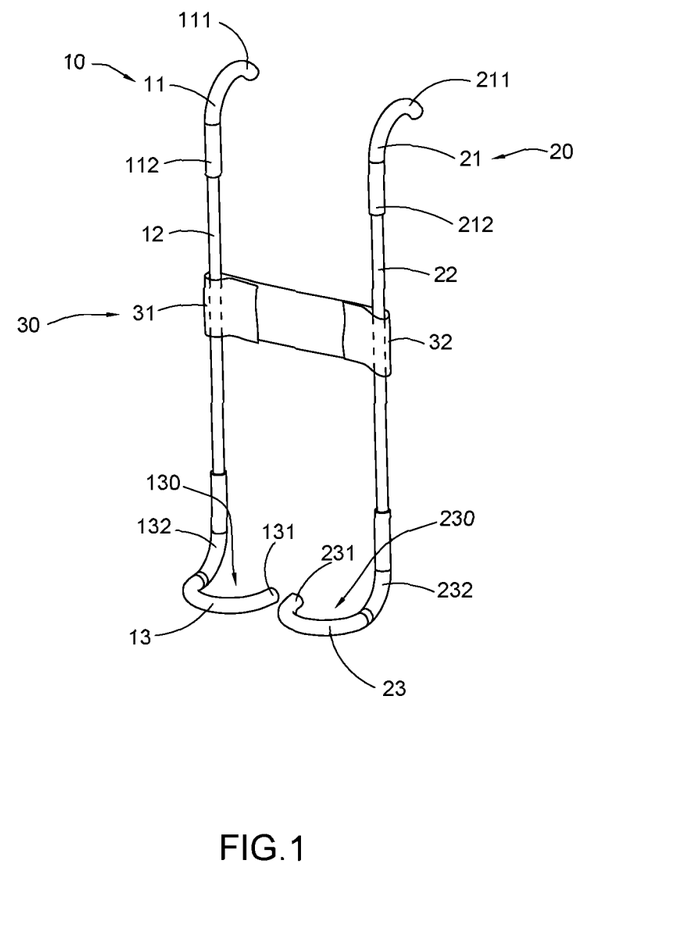
FIG. 1 is a perspective view of an upright posture retainer for upper body according to a preferred embodiment of the present invention.
Figure 2:
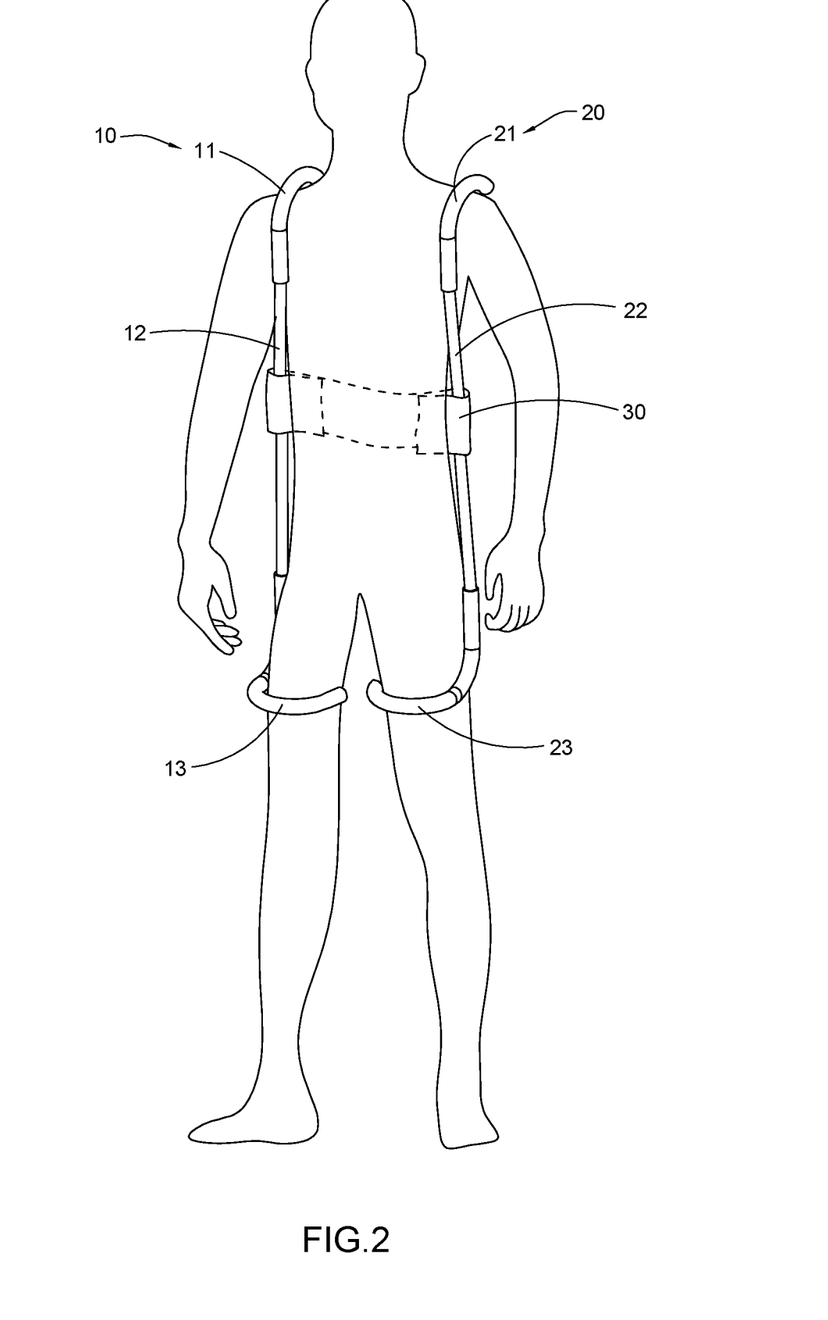
FIG. 2 is a perspective view of the upright posture retainer for upper body according to the preferred embodiment of the present invention.
Figure 3:
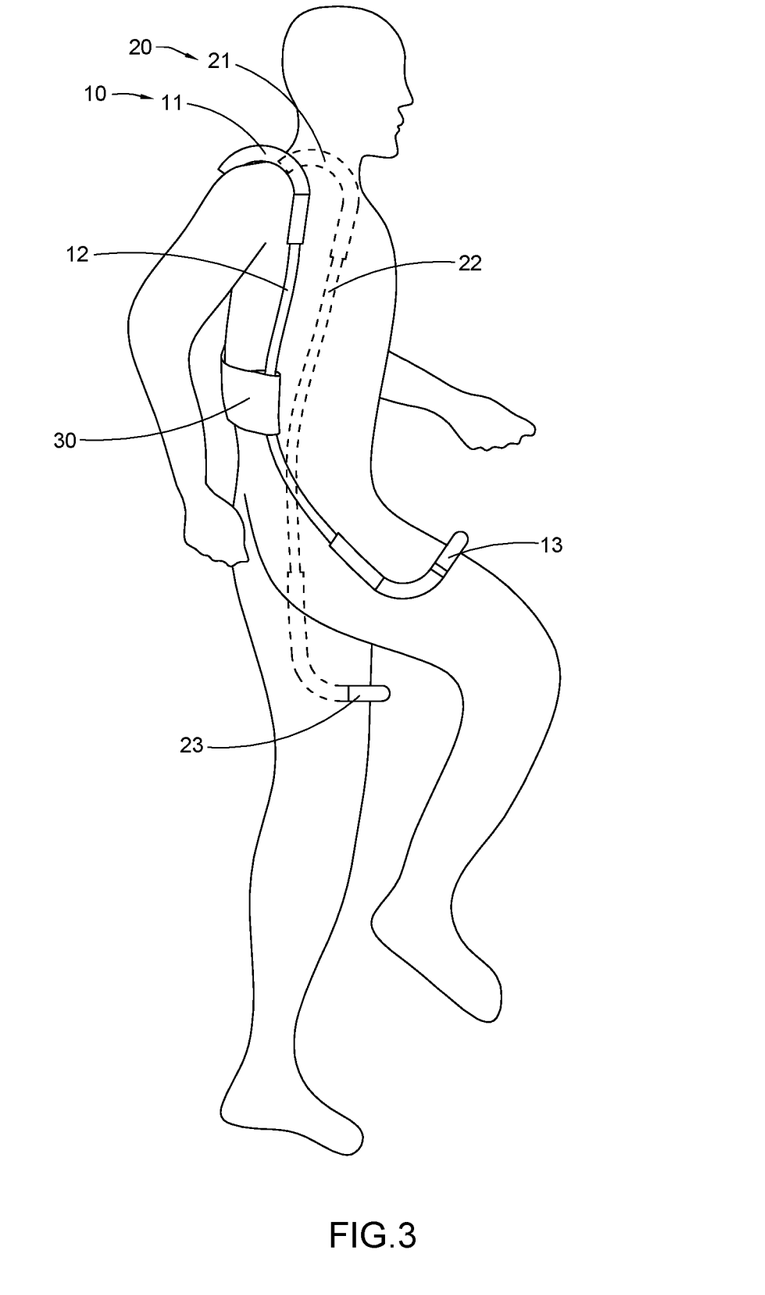
FIG. 3 is a perspective view of the upright posture retainer for upper body according to the preferred embodiment of the present invention.

Referring to FIG. 1 to FIG. 3 of the drawings, an exercise device that can also works as an upright posture retainer for upper body according to a preferred embodiment is illustrated, referring to upright posture retainer for upper body hereinafter, wherein the upright posture retainer for upper body comprises a first upright retaining frame 10, a second upright retaining frame 20 and an adjusting device 30. The upright posture retainer for upper body retains human body in an upright posture.

The first upright retaining frame 10 and the second upright retaining frame 20 are connected by the adjusting device 30. A distance between the first upright retaining frame 10 and the second upright retaining frame 20 is adjusted by the adjusting device 30. According to the preferred embodiment, the adjusting device 30 is implemented as a belt with loop and hook fasteners (Velcro). One skilled in the art will understand that the adjusting device 30 being implemented as the belt with Velcro of the preferred embodiment of the present invention as shown in the drawings and described above is exemplary only and not intended to be limiting.

According to the preferred embodiment of the present invention, the structure of first upright retaining frame 10 and the structure of the second upright retaining frame 20 are symmetrical longitudinally.

Specifically, the first upright retaining frame 10 further comprises a first shoulder retaining member 11, a first resilient longitudinal retaining frame 12 and a first leg retaining frame 13. The first resilient longitudinal retaining frame 12 is extended longitudinally. The first shoulder retaining member 11 is longitudinally extended from one end of the first resilient longitudinal retaining frame 12 and then is transversely extended to form a curved end in such a manner that the shape of the first shoulder retaining member 11 is matched with the shape of the human shoulder, so that the first shoulder retaining member 11 is hanged over the human shoulder, thereby the first upright retaining frame 10 hanging on and contacting with the front of human body. In other words, one end 112 of the first shoulder retaining member 11 is longitudinally extended from the first resilient longitudinal retaining frame 12 and other end 111 of the first shoulder retaining member 11 is transversely extended to form a first shoulder contacting space 110 between the end 112 and 111 in such a manner that the end 112 of the first shoulder retaining member 11 is contacted with the front of the human shoulder, so that the curvature of the first shoulder contacting space 110 is matched with the human shoulder, thereby the first shoulder retaining member 11 being affixed to the human shoulder and the first upright retaining frame 10 being attaching to upper human body. It is worth mentioning that the first shoulder retaining member 11 is enclosed with cushions, so that the first shoulder retaining member 11 has a cushioning effect with the human shoulder and the human shoulder is prevented from being scratching caused by force of friction between the first shoulder retaining member 11 and the human shoulder.

As mentioned above, the structure of first upright retaining frame 10 and the structure of the second upright retaining frame 20 are mirror symmetrical, the first upright retaining frame 10 and the second upright retaining frame 20 have similar structures. In the preferred embodiment, the second upright retaining frame 20 further comprises a second shoulder retaining member 21, a second resilient longitudinal retaining frame 22 and a second leg retaining frame 23.

Each of the first and second resilient longitudinal retaining frames 12, 22 is made of resilient material with good rigidity and toughness and is capable of tending to recover the original upright state under bending stress. Each of the first and second resilient longitudinal retaining frames 12, 22 is capable of being bent up to 90 degrees or more. Each of the first and resilient longitudinal retaining frames 12, 22 crosses through one end portion 31, 32 of the adjusting device 30. In this preferred embodiment, the adjusting device 30 is implemented as a belt with the loop and hook fasteners, not only the length of the adjusting device 30 is adjustable so as to adjust the distance between the first upright retaining frame 10 and the second upright retaining frame 20, but also the tightness of the end portions 31, 32 of the adjusting device 30 sheathed with the first and second resilient longitudinal retaining frames 12, 22 and the position of the adjusting device 30 on the first and second resilient longitudinal retaining frames 12, 22 are adjustable, so that the adjusting device 30 is capable of being contacting with the back and waist of human upper body.

The first leg retaining frame 13 is extended from one end of the first resilient longitudinal retaining frame 12 and then is transversely extended to form a semicircular end in such a manner that the shape of the first leg retaining frame 13 is matched with the shape of the human leg. The first leg retaining frame 13 is arranged on the front of the human leg and the first leg retaining frame 13 is connected with the first resilient longitudinal retaining frame 12, when the human leg applies force toward resulting from the contractions of the front leg muscles, the first leg retaining frame 13 gives the human leg a reverse force to against the forward force that the human leg applied, so that the human upper body is retained upright and the front leg muscles are exercised and strengthened. In other words, one end 132 of the first leg retaining frame 13 is extended from the first resilient longitudinal retaining frame 12 and other end 131 of the first leg retaining frame 13 is transversely extended to form a first leg retaining space 130 between the end 132 and 131 in such a manner that the first leg retaining frame 13 is contacted with the front of the human leg, so that the curvature of the first leg retaining space 130 is matched with the human leg. It is worth mentioning that the first leg retaining frame 13 is enclosed with cushions, so that the first leg retaining frame 13 has a cushioning effect with the human leg and the human leg is prevented from being scratching caused by force of friction between the first leg retaining frame 13 and the human leg.

It is worth mentioning that in other embodiment, the first leg retaining frame 13 is also enclosed with cushions.

According to the preferred embodiment, the first shoulder retaining member 11 of the first upright retaining frame 10 and the second shoulder retaining member 21 of the second upright retaining frame 20 have similar structures. The first resilient longitudinal retaining frame 12 of the first upright retaining frame 10 and the second resilient longitudinal retaining frame 22 of the second upright retaining frame 20 have similar structures. The structure of the first leg retaining frame 13 of the first upright retaining frame 10 and the structure of the second leg retaining frame 23 of the second upright retaining frame 20 are mirror symmetrical.

Specifically, the second resilient longitudinal retaining frame 22 is extended longitudinally. The second shoulder retaining member 21 is longitudinally extended from one end of the second resilient longitudinal retaining frame 22 and then is transversely extended to form a curved end in such a manner that the shape of the second shoulder retaining member 21 is matched with the shape of the human shoulder, so that the second shoulder retaining member 21 is hanged over the human shoulder, thereby the second upright retaining frame 20 hanging on and contacting with the front of human body. In other words, one end 212 of the second shoulder retaining member 21 is longitudinally extended from the second resilient longitudinal retaining frame 22 and other end 211 of the second shoulder retaining member 21 is transversely extended to form a second shoulder contacting space 210 between the end 212 and 211 in such a manner that the end 212 of the second shoulder retaining member 21 is contacted with the front of the human shoulder, so that the curvature of the second shoulder contacting space 210 is matched with the human shoulder, thereby the second shoulder retaining member 21 being affixed to the human shoulder and the second upright retaining frame 20 being attaching to upper human body. It is worth mentioning that the second shoulder retaining member 21 is enclosed with cushions, so that the second shoulder retaining member 21 has a cushioning effect with the human shoulder and the human shoulder is prevented from being scratching caused by force of friction between the second shoulder retaining member 21 and the human shoulder.

As mentioned above, the second resilient longitudinal retaining frame 22 is made of resilient material with good rigidity and toughness and is capable of tending to recover the original upright state under bending stress. The second resilient longitudinal retaining frame 22 is capable of being bent up to 90 degrees or more. The second resilient longitudinal retaining frame 22 crosses through other end portion 32 of the adjusting device 30. In this preferred embodiment, the adjusting device 30 is implemented as a belt with Velcro, not only the length of the adjusting device 30 is adjustable so as to adjust the distance between the first upright retaining frame 10 and the second upright retaining frame 20, but also the tightness of the other end portion 32 of the adjusting device 30 sheathed with the second resilient longitudinal retaining frame 22 and the position of the adjusting device 30 on the second resilient longitudinal retaining frame 22 are adjustable, so that the adjusting device 30 is capable of being contacting with the back and waist of human upper body.

The second leg retaining frame 23 is extended from one end of the second resilient longitudinal retaining frame 22 and then is transversely extended to form a semicircular end in such a manner that the shape of the second leg retaining frame 23 is matched with the shape of the human leg. The second leg retaining frame 23 is arranged on the front of the human leg and the second leg retaining frame 23 is connected with the second resilient longitudinal retaining frame 22, when the human leg applies force toward resulting from the contractions of the front leg muscles, the second leg retaining frame 23 gives the human leg a reverse force to against the forward force that the human leg applied, so that the human upper body is retained upright and the front leg muscles are exercised and strengthened. In other words, one end 232 of the second leg retaining frame 23 is extended from the second resilient longitudinal retaining frame 22 and other end 231 of the first leg retaining frame 23 is transversely extended to form a second leg retaining space 230 between the end 232 and 231 in such a manner that the second leg retaining frame 23 is contacted with the front of the human leg, so that the curvature of the second leg retaining space 230 is matched with the human leg. It is worth mentioning that the second leg retaining frame 23 is enclosed with cushions, so that the second leg retaining frame 23 has a cushioning effect with the human leg and the human leg is prevented from being scratching caused by force of friction between the second leg retaining frame 23 and the human leg.

It is worth mentioning that in other embodiment, the second leg retaining frame 23 is also enclosed with cushions.

In other words, the extending direction of the first leg retaining frame 13 from the first resilient longitudinal retaining frame 12 is opposite to the extending direction of the second leg retaining frame 23 from the second resilient longitudinal retaining frame 22. The first leg retaining space 130 formed by the first leg retaining frame 13 and the second leg retaining space 230 formed by the second leg retaining frame 23 both are provided between the first resilient longitudinal retaining frame 12 and the second resilient longitudinal retaining frame 22, so that the first leg retaining frame 13 of the first upright retaining frame 10 and the second leg retaining frame 23 of the second upright retaining frame 20 from mirror symmetrical structures.

It is worth mentioning that the shape of the first leg retaining frame 13 and the second leg retaining frame 23 mentioned above is exemplary only and not intended to be limiting. In other embodiments, the first leg retaining frame 13 and the second leg retaining frame 23 are able to be implemented as other arc-shaped structures and spiral-shaped structures so as to respectively form the first leg retaining space 130 and the second leg retaining space 230, so that the first leg retaining frame 13 and the second leg retaining frame 23 have opposite acting forces with the leg muscles. As shown in FIG. 3 of the drawings, the first leg retaining frame 13 and the protected 23 are contacted with the front of human legs and provide opposite acting forces against the human legs; the first resilient longitudinal retaining frame 12 and the second resilient longitudinal retaining frame 22 remain upright and the first shoulder retaining member 11 and the second shoulder retaining member 21 hang over human shoulders; the adjusting device 30 retains a distance between the first resilient longitudinal retaining frame 12 and the second resilient longitudinal retaining frame 22 and protects the human upper body; so that the human upper body is protected and is retained upright, thereby the leg muscles being exercised.

It is worth mentioning that the first upright retaining frame 10 is able to be integrally formed and is also to be respectively formed and then connected together. Similarly, the second upright retaining frame 20 is able to be integrally formed and is also to be respectively formed and then connected together.

It is worth mentioning that the first upright retaining frame 10 and the second upright retaining frame 20 are able to be completely covered with cushions and are also able to be partially covered with cushions, especially the positions where the force of friction respectively generated between the first upright retaining frame 10 and the second upright retaining frame 20 with the human body.

Referring to FIG. 4 to FIG. 8 and FIG. 10 of the drawings, an upright posture retainer for upper body according to a first alternative mode of the preferred embodiment is illustrated, wherein the upright posture retainer for upper body comprises a first upright retaining frame 10', a second upright retaining frame 20' and an adjusting device 30'.

The first upright retaining frame 10' further comprises a first shoulder retaining member 11', a first resilient longitudinal retaining frame 12' and a first leg retaining frame 13'. One end 112' of the first shoulder retaining member 11' is longitudinally extended from the first resilient longitudinal retaining frame 12' and other end 111' of the first shoulder retaining member 11' is transversely extended to form a first shoulder contacting space 110' between the end 112' and 111' in such a manner that the end 112' of the first shoulder retaining member 11' is contacted with the rear of the human shoulder, so that the curvature of the first shoulder contacting space 110' is matched with the human shoulder, thereby the first shoulder retaining member 11' being affixed to the human shoulder and the first resilient longitudinal retaining frame 12' being attaching to the rear of the upper human body. one end 132' of the first leg retaining frame 13' is extended from the first resilient longitudinal retaining frame 12' and other end 131' of the first leg retaining frame 13' is transversely extended to form a first leg retaining space 130' between the end 132' and 131' in such a manner that the first leg retaining frame 13' is contacted with the front of the human leg, so that the curvature of the first leg retaining space 130' is matched with the human leg. It is worth mentioning that partial portion of the first resilient longitudinal retaining frame 12' is enclosed with a first outer cushion layer 41'.

The second upright retaining frame 20' further comprises a second shoulder retaining member 21', a second resilient longitudinal retaining frame 22' and a second leg retaining frame 23'. One end 212' of the second shoulder retaining member 21' is longitudinally extended from the second resilient longitudinal retaining frame 22' and other end 211' of the second shoulder retaining member 21' is transversely extended to form a second shoulder contacting space 210' between the end 212' and 211' in such a manner that the end 212' of the second shoulder retaining member 21' is contacted with the rear of the human shoulder, so that the curvature of the second shoulder contacting space 210' is matched with the human shoulder, thereby the second shoulder retaining member 21' being affixed to the human shoulder and the second resilient longitudinal retaining frame 22' being attaching to the rear of the upper human body. one end 232' of the second leg retaining frame 23' is extended from the second resilient longitudinal retaining frame 22' and other end 231' of the second leg retaining frame 23' is transversely extended to form a second leg retaining space 230' between the end 232' and 231' in such a manner that the second leg retaining frame 23' is contacted with the front of the human leg, so that the curvature of the second leg retaining space 230' is matched with the human leg. It is worth mentioning that partial portion of the second resilient longitudinal retaining frame 22' is enclosed with a second outer cushion layer 42'.

Figure 4:
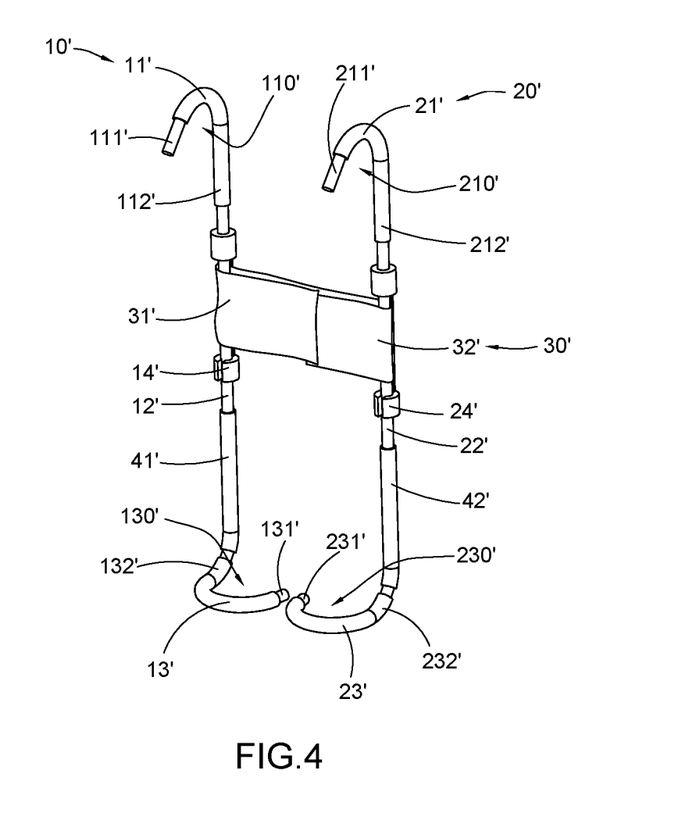
FIG. 4 is a perspective view of an upright posture retainer for upper body according to a first alternative mode of the preferred embodiment of the present invention.
Figure 5:
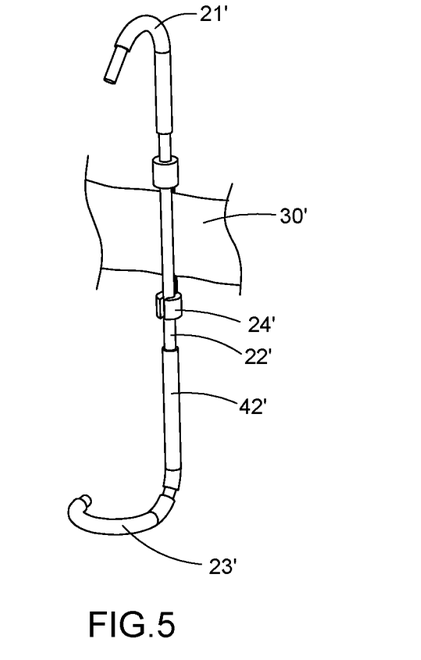
FIG. 5 is a partial enlarged view of the upright posture retainer for upper body according to the first alternative mode of the preferred embodiment of the present invention.

According to the first alternative mode of the present invention, the first upright retaining frame 10' further comprises a first positioning member 14' fixed on the first resilient longitudinal retaining frame 12' and the second upright retaining frame 20' further comprises a second positioning member 24' fixed on the second resilient longitudinal retaining frame 22'. One end 31' of the adjusting device 30' is positioned between a gap formed by the first resilient longitudinal retaining frame 12' and the first positioning member 14'. Other end 32' of the adjusting device 30' is positioned between a gap formed by the second resilient longitudinal retaining frame 22' and the second positioning member 24'. One skilled in the art will understand that the first positioning member 14' and the second positioning member 24' in the embodiment of the present invention as shown in the drawings and described above is exemplary only and not intended to be limiting.

Figure 6:
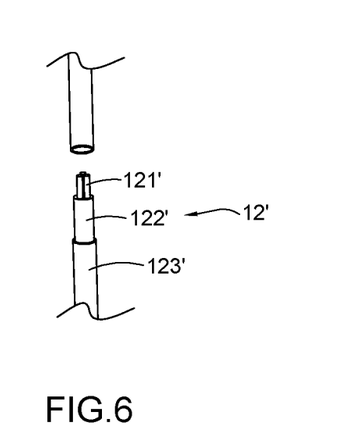
FIG. 6 is a partial enlarged view of the upright posture retainer for upper body according to the first alternative mode of the preferred embodiment of the present invention.

As shown in FIG. 6, the first resilient longitudinal retaining frame 12' further comprises an inner resilient frame 121', a middle enhancing layer 122' covering around the inner resilient frame 121' and an outer malleable layer 123' covering around the middle enhancing layer 122' in such a manner that the first resilient longitudinal retaining frame 12' has good rigidity and toughness and is capable of tending to recover the original upright state under stress. One skilled in the art will understand that the second resilient longitudinal retaining frame 22' has the similar inner structure with the first resilient longitudinal retaining frame 12'.

Figure 7:
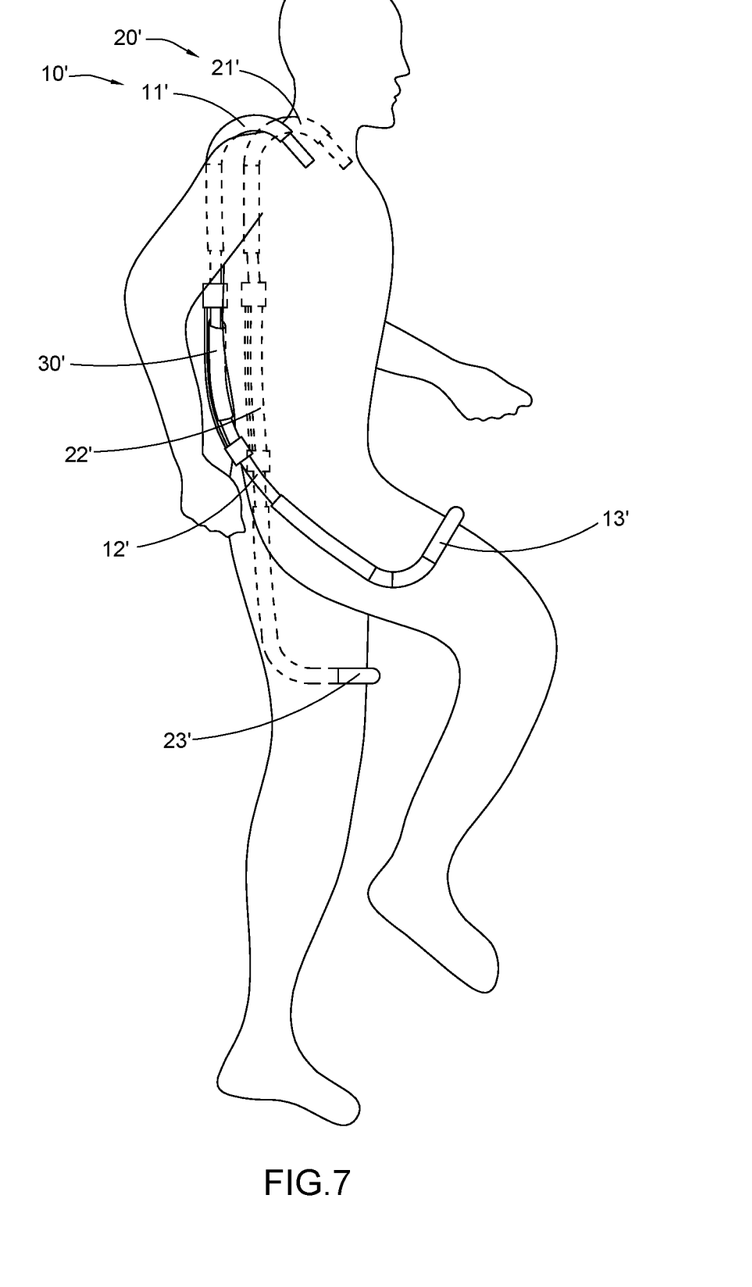
FIG. 7 is a perspective view of the upright posture retainer for upper body according to the first alternative mode of the preferred embodiment of the present invention.

As shown in FIG. 7 of the drawings, the first leg retaining frame 13' and the protected 23' are contacted with the front of human legs and provide opposite acting forces against the human legs; the first resilient longitudinal retaining frame 12' and the second resilient longitudinal retaining frame 22' remain upright and are contacted with the human back and waist such that the human upper body is remained in an upright posture; the first shoulder retaining member 11' and the second shoulder retaining member 21' hang over the human shoulders; the adjusting device 30' retains a distance between the first resilient longitudinal retaining frame 12' and the second resilient longitudinal retaining frame 22' and protects the human upper body; so that the human upper body is protected and is retained upright, thereby the leg muscles being exercised.

Figure 8:
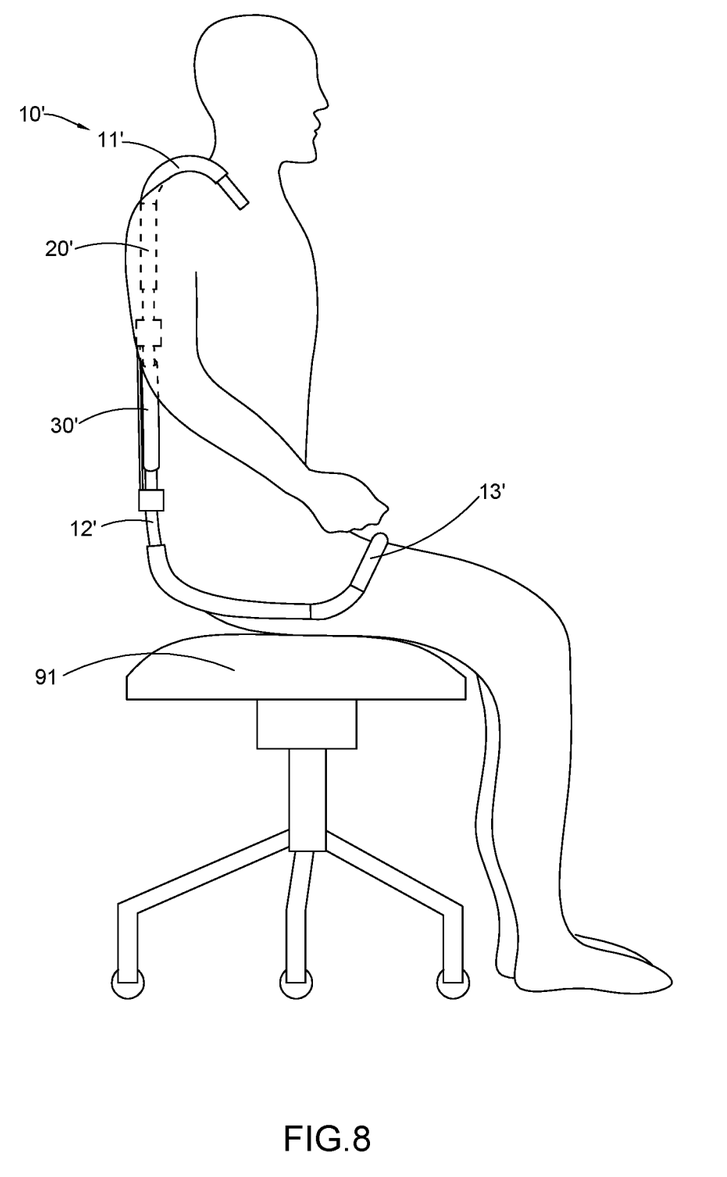
FIG. 8 is a perspective view of the upright posture retainer for upper body according to the first alternative mode of the preferred embodiment of the present invention.

It is worth mentioning that the upright posture retainer for upper body of the present invention is not only used as a convenient and portable exercise equipment, but also used as a seating position equipment and a backrest. As shown in FIG. 8 of the drawings, when a person seats on a chair 91 without a chair back, the first shoulder retaining member 11' and the first resilient longitudinal retaining frame 12' are respectively hanged over the human shoulder, the first leg retaining frame 13' and the second leg retaining frame 23' are contacted with the front of the human legs, and the adjusting device 30' is contacted with the back and waist of the person. On one hand, as the first resilient longitudinal retaining frame 12' and the second resilient longitudinal retaining frame 22' are capable of being bent no more than 90 degrees and have resilient function to retain upright, when the person tends to hunch, the first leg retaining frame 13' and the second leg retaining frame 23' are capable of applying reactive force on the front of the legs so as to prevent the person from hunching, thereby the upright posture retainer for upper body of the present invention being used as a seating position equipment. On the other hand, when the person seats on the chair 91 without a chair back, the first resilient longitudinal retaining frame 12' and the second resilient longitudinal retaining frame 22' provide a support functioned as the chair back, thereby the upright posture retainer for upper body of the present invention being used as a chair back.

Figure 10:
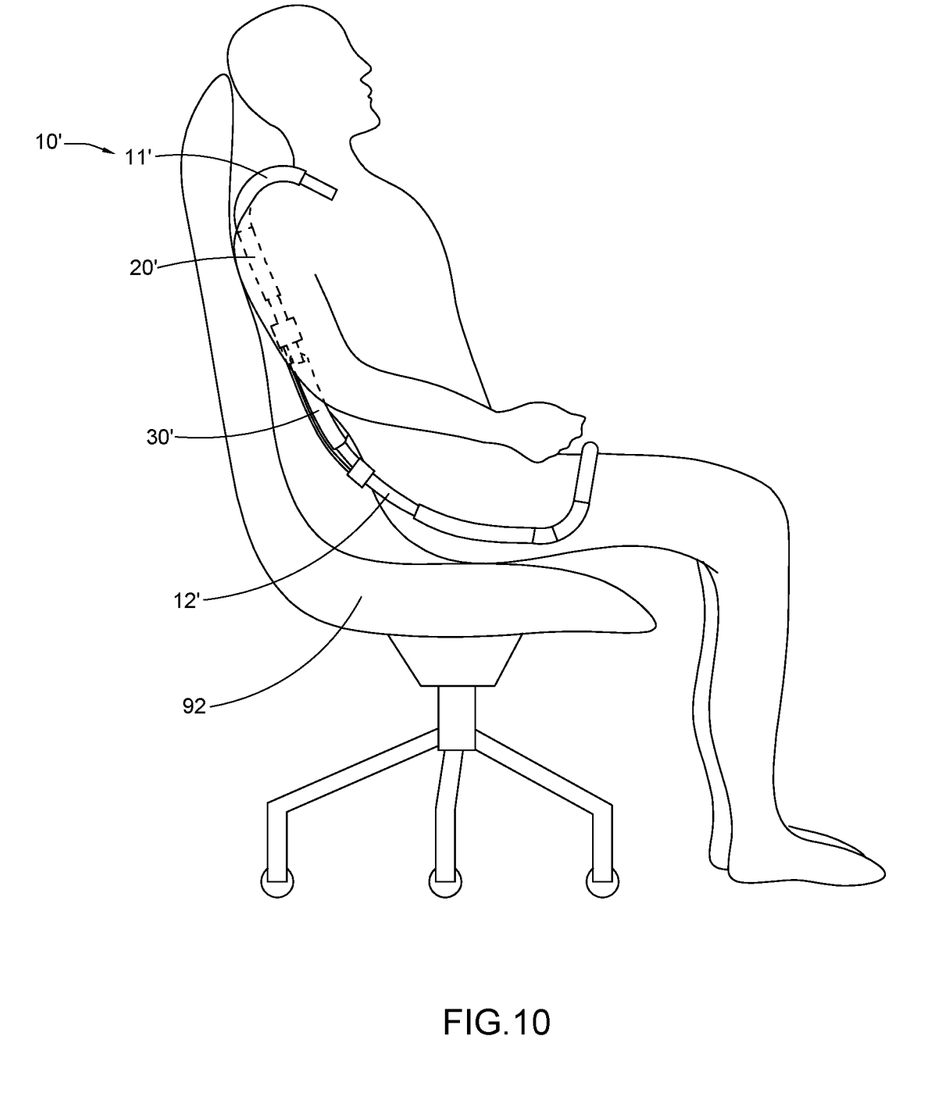
FIG. 10 is a perspective view of the upright posture retainer for upper body according to the first alternative mode of the preferred embodiment of the present invention.

It is worth mentioning that the upright posture retainer for upper body of the present invention is not only used as a convenient and portable exercise equipment, a seating position equipment and a backrest, but also used as a nap assisting equipment. As shown in FIG. 10 of the drawings, when a person seats on a chair 92 with a chair back, the first shoulder retaining member 11' and the first resilient longitudinal retaining frame 12' are respectively hanged over the human shoulder, the first leg retaining frame 13' and the second leg retaining frame 23' are contacted with the front of the human legs, and the adjusting device 30' is contacted with the back and waist of the person. As the first resilient longitudinal retaining frame 12' and the second resilient longitudinal retaining frame 22' are made of resilient material with good rigidity and toughness and are capable of tending to recover the original upright state under stress, the adjusting device 30', the first resilient longitudinal retaining frame 12' and the second resilient longitudinal retaining frame 22' provide supports for the entire back and waist of human upper body, so that the back and waist of human upper body are not hanged in the air and are relieved even through there is a gap between the back and waist of human upper body with the chair back of the chair 92, thereby the upright posture retainer for upper body of the present invention being used as nap assisting equipment, especially for office workers.

Figure 9:
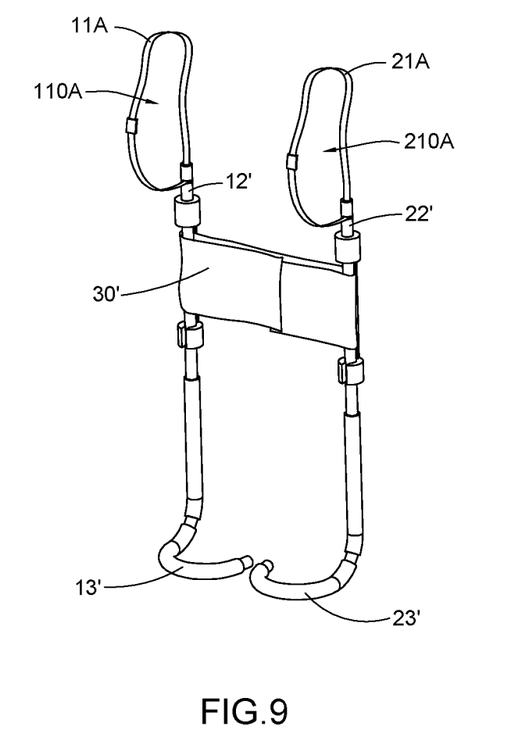
FIG. 9 is a perspective view of an upright posture retainer for upper body according to a second alternative mode of the preferred embodiment of the present invention.

Referring to FIG. 9 of the drawings, an upright posture retainer for upper body according to a second alternative mode of the preferred embodiment is illustrated. Compared with the upright posture retainer for upper body according to the first alternative mode of the preferred embodiment, in the second alternative mode, the main difference is the first shoulder retaining member and the second shoulder retaining member. According to the first alternative mode, the first shoulder retaining member 11' and the second shoulder retaining member 21' are implemented as rods; while according to the second alternative mode, the first shoulder retaining member 11A form the first shoulder contacting space 110A and the second shoulder retaining member 21A forming the second shoulder contacting space 210A are implemented as flexible shoulder straps. The flexible shoulder straps are more comfortable for human shoulders.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An exercise device and upright posture retainer for a user, comprising:

two upright retaining frames, and an adjusting device having two end portions connected to said upright retaining frames respectively, wherein said adjusting device is arranged to adjust a distance between said upright retaining frames, wherein each of said upright retaining frames comprises a resilient longitudinal retaining frame extended longitudinally and tending to recover an original upright state under bending stress, a shoulder retaining member arranged for hanging at shoulders of the user and a leg retaining frame for retaining at legs of the user, wherein said shoulder retaining member is extended from an upper end of said resilient longitudinal retaining frame so as to form a shoulder contacting space, wherein said leg retaining frame is extended from a lower end of said resilient longitudinal retaining frame and transversely extended to form a leg retaining space, wherein said adjusting device is fixed to said resilient longitudinal retaining frames of said upright retaining frames for being supported at a back of the user, wherein each of said upright retaining frames further comprises a positioning member fixed on said resilient longitudinal retaining frame, wherein two ends of said adjusting device are respectively positioned on said positioning members of said upright retaining frames.

2. The exercise device and upright posture retainer, as recited in claim 1, wherein said leg retaining frame is extended from said lower end of said resilient longitudinal retaining frame and then is transversely extended to form an arc-shaped end defined said leg retaining space.

3. The exercise device and upright posture retainer, as recited in claim 1, wherein said leg retaining frame has a semicircular shape, wherein said leg retaining frames of said upright retaining frames are mirror symmetrical, wherein said leg retaining frames of said upright retaining frames are extended inwardly and face-to-face.

4. The exercise device and upright posture retainer, as recited in claim 1, wherein said leg retaining frame is vertical to said resilient longitudinal retaining frame.

5. The exercise device and upright posture retainer, as recited in claim 1, wherein said shoulder retaining member is longitudinally extended from one end of said resilient longitudinal retaining frame and then is transversely extended to form said shoulder contacting space.

6. The exercise device and upright posture retainer, as recited in claim 1, wherein one end of said shoulder retaining member is longitudinally extended from said resilient longitudinal retaining frame and other end of said shoulder retaining member is transversely extended to form said shoulder contacting space.

7. The exercise device and upright posture retainer, as recited in claim 1, wherein said shoulder retaining member is an arc-shaped rod.

8. The exercise device and upright posture retainer, as recited in claim 1, wherein said shoulder retaining member comprises flexible shoulder straps.

9. The exercise device and upright posture retainer, as recited in claim 1, wherein said adjusting device is a belt with hook and loop fasteners.

10. The exercise device and upright posture retainer, as recited in claim 1, wherein said resilient longitudinal retaining frame further comprises an inner resilient frame, a middle covering layer covering around said inner resilient frame and an outer malleable layer covering around said middle covering layer in such a manner that said first resilient longitudinal retaining frame is configured to recover said original upright state under stress.

11. The exercise device and upright posture retainer, as recited in claim 1, wherein said resilient longitudinal retaining frame further comprises an inner resilient frame, a middle covering layer covering around said inner resilient frame and an outer malleable layer covering around said middle covering layer in such a manner that said first resilient longitudinal retaining frame is configured to recover said original upright state under stress.

12. An exercise device and upright posture retainer for a user, comprising:
two upright retaining frames, and
an adjusting device having two end portions connected to said upright retaining frames respectively, wherein said adjusting device is arranged to adjust a distance between said upright retaining frames, wherein each of said upright retaining frames comprises a resilient longitudinal retaining frame extended longitudinally and tending to recover an original upright state under bending stress, a shoulder retaining member arranged for hanging at shoulders of the user and a leg retaining frame for retaining at legs of the user, wherein said shoulder retaining member is extended from an upper end of said resilient longitudinal retaining frame so as to form a shoulder contacting space, wherein said leg retaining frame is extended from a lower end of said resilient longitudinal retaining frame and transversely extended to form a leg retaining space, wherein said adjusting device is fixed to said resilient longitudinal retaining frames of said upright retaining frames for being supported at a back of the user, wherein each of said upright retaining frames further comprises a positioning member fixed on said resilient longitudinal retaining frame, wherein a gap is formed between said positioning member and said resilient longitudinal retaining frame, wherein said adjusting device crosses through said gaps.

13. The exercise device and upright posture retainer, as recited in claim 12, wherein said leg retaining frame is extended from said lower end of said resilient longitudinal retaining frame and then is transversely extended to form an arc-shaped end defined said leg retaining space.

14. The exercise device and upright posture retainer, as recited in claim 12, wherein said leg retaining frame has a semicircular shape, wherein said leg retaining frames of said upright retaining frames are mirror symmetrical, wherein said leg retaining frames of said upright retaining frames are extended inwardly and face-to-face.

15. The exercise device and upright posture retainer, as recited in claim 12, wherein said leg retaining frame is vertical to said resilient longitudinal retaining frame.

16. The exercise device and upright posture retainer, as recited in claim 12, wherein said shoulder retaining member is longitudinally extended from one end of said resilient longitudinal retaining frame and then is transversely extended to form said shoulder contacting space.

17. The exercise device and upright posture retainer, as recited in claim 12, wherein one end of said shoulder retaining member is longitudinally extended from said resilient longitudinal retaining frame and other end of said shoulder retaining member is transversely extended to form said shoulder contacting space.

18. The exercise device and upright posture retainer, as recited in claim 12, wherein said shoulder retaining member is an arc-shaped rod.

19. The exercise device and upright posture retainer, as recited in claim 12, wherein said shoulder retaining member comprises flexible shoulder straps.

20. The exercise device and upright posture retainer, as recited in claim 12, wherein said adjusting device is a belt with hook and loop fasteners.

* * * * *